United States Patent [19]

Nishioka et al.

[11] 4,415,240
[45] Nov. 15, 1983

[54] ILLUMINATION OPTICAL SYSTEM FOR AN ENDOSCOPE

[75] Inventors: Kimihiko Nishioka; Nobuo Yamashita, both of Hachioji, Japan

[73] Assignee: Olympus Optical Co., Ltd., Tokyo, Japan

[21] Appl. No.: 171,759

[22] Filed: Jul. 24, 1980

[30] Foreign Application Priority Data

Jul. 27, 1979 [JP] Japan .................................. 54/95720

[51] Int. Cl.³ .......................... G02B 5/14; G02B 23/00
[52] U.S. Cl. .................................. 350/442; 350/96.10
[58] Field of Search ................. 350/96.10, 442; 362/32

[56] References Cited

U.S. PATENT DOCUMENTS

2,589,569  3/1952  Peter et al. ...................... 350/96.10
3,157,089  11/1964  Menefee .......................... 350/96.10

*Primary Examiner*—John K. Corbin
*Assistant Examiner*—Rebecca D. Gass
*Attorney, Agent, or Firm*—Cushman, Darby & Cushman

[57] ABSTRACT

An illumination optical system for an endoscope in which, by arranging a cylindrical reflection member between a light guide and a lens system, a distribution curve of luminous intensity is improved with the effective utilization of illumination light and yet the formation of the image of the light guide end face on the object surface is obviated, thereby enabling attainment of a uniform illumination over the object surface.

13 Claims, 17 Drawing Figures

ILLUMINATION OPTICAL SYSTEM FOR AN ENDOSCOPE

BACKGROUND OF THE INVENTION (a) Field of the Invention

The present invention relates to a wide angle illumination optical system for an endoscope which makes possible utilization of illumination light without waste.

(b) Description of the Prior Art

Figure 1:
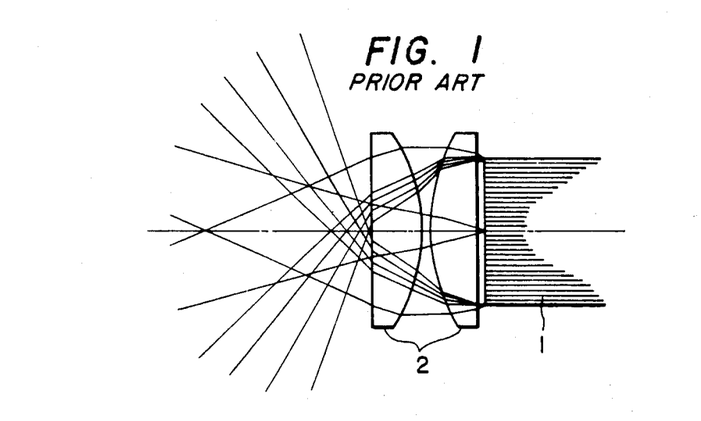
FIG. 1 shows a structure of an illumination optical system for conventional wide angle endoscopes.
Figure 2:
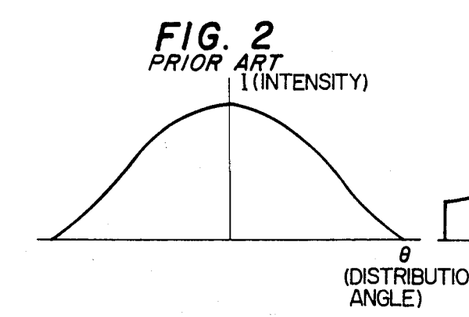
FIG. 2 shows a distribution curve of luminous intensity of the above optical system.
Figure 3:
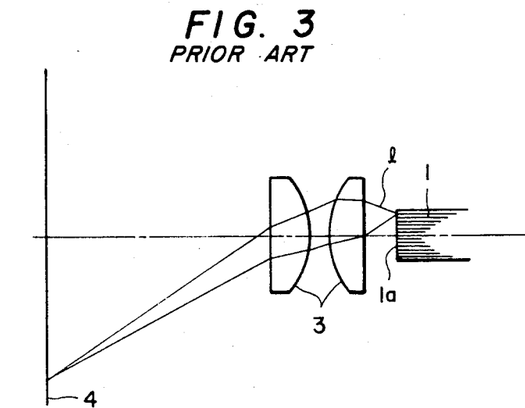
FIG. 3 shows a structure of an illumination optical system of the projection type.
Figure 4:
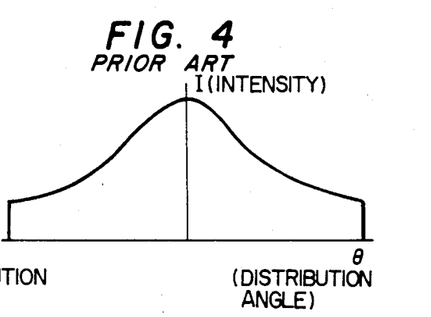
FIG. 4 shows a distribution curve of luminous intensity of the optical system as shown in FIG. 3.
Figure 5:
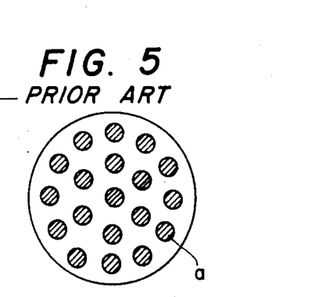
FIG. 5 is an illustration of the illumination light on the object surface in the case of use of the optical system as shown in FIG. 3.

Since endoscopes of recent years have been equipped with wider angled observation system, it has become necessary that the illumination system therefor should also be of wider angle. The wider angle illumination system shown in FIG. 1, as an example, which has been developed from the above mentioned necessity, has been known. In this illumination system, a positive lens system 2 is disposed in front of a light guide 1 comprising an optical fiber bundle. In this arrangement, the illumination light coming from the light guide 1 is once converged and then dispersed by the positive lens 2 and, by utilizing this dispersed light, it has been made possible to obtain a wide angle illumination. However, illumination by this illumination system has a drawback in that a peripheral portion of the visual field lacks light. The reason for this is that in the case of such an illumination system the distribution curve of luminous intensity is as shown in FIG. 2 and, as the illumination angle becomes wider the light intensity becomes smaller and gradually reaches zero. Therefore, the effective illumination field in such an illumination system is narrower than the extent where the illumination light reaches. The portion which lacks light is in almost the same condition as the case in which no illumination light is present even if the illumination light has in fact reached there and, therefore, the light present at that portion is in effect wasted. As a method to remove such a drawback, an illumination method by which an exit end face of the light guide is projected (hereinafter referred to as "a projection type") is available. Accordingly to this method, an image of the exit end face 1a of the light guide 1 is formed on the object surface 4 by the lens 3 as shown in FIG. 3. In this example, the lens 3 is so selected that the size of the image of the light guide exit end face corresponds to that of the observation visual field and is so arranged to remove a parallax (as known, there exists a parallax since an image guide and a light guide are disposed side by side in an endoscope), and thus the observation visual field is completely illuminated and yet the illumination light does not reach areas other than the observation visual field and, therefore, no wasted light is present. Furthermore, since the exit end face of the light guide is projected, the distribution curve of luminous intensity is as shown in FIG. 4 and a certain luminous intensity is obtained even at the widest angle of view. Therefore, observation is possible over the entire area which the illumination covers and thus the illumination field and the visual field are coextensive. Further, the fact that the illumination light does not reach areas other than the observation field is advantageous not only in obviating waste of the illumination light but also in avoiding such an occurrence that the reflection light outside the visual field may form ghosts, etc. upon entering into the observation system causing a lack of clarity in the performance of observation. However, there are some defects in such a method as explained below. The exit end face of the fiber bundle as a whole does not uniformly illuminate but only the core portions of the respective fibers illuminate. Since the end face of the fiber is projected in its state onto the object surface, the object surface is illuminated with only the core portions being lit in patterns as illustrated in FIG. 5, that is, the object surface is illuminated as if it were covered by a net, which renders it extremely difficult to conduct a proper observation of the object. In practice, the net-pattern is blurred to some extent by virtue of the lens aberrations or other factors but such condition is not sufficient for carrying out the observation.

SUMMARY OF THE INVENTION

An object of the present invention is to provide an illumination optical system for an endoscope in which, by arranging a cylindrical reflection member between a light guide and a lens system, a distribution curve of luminous intensity is improved with the effective utilization of illumination light and yet the formation of the image of the light guide end face on the object surface is obviated, thereby enabling attainment of a uniform illumination over the object surface.

The invention will be described further by way of examples, with reference to the accompanying drawings.

In order to achieve the uniform illumination which is one of the objects of the present invention, the image of the light guide end face may be blurred so that a net-pattern does not appear on the object surface in such an illumination method of the projection type as explained above. However, when the image is blurred, the distribution curve of its luminous intensity tends to be closer to the curve shown in FIG. 2 and, for this reason, there occurs a loss in illumination light causing a peripheral portion of the visual field to lack light. Further, in order to blur the image, the light guide 1 may be moved from the position in FIG. 3 to that in FIG. 6 but, in this case, an outward ray 1' is outwardly deviated from the lens and cannot be effective as the illumination light. Furthermore, there occur some rays, such as ray 1", which are cut by a peripheral surface portion 3a of the lens. A means by which such occurrence could be prevented would be to make the diameter of the lens larger, but such a means is inappropriate to the illumination system for an endoscope which requires the system to be slender. Such a method by which it is attempted to erase the net-pattern by means of blurring an image is undesirable since the greater the extent of the blur is, the lesser are the merits of the projection type illumination system.

Figure 6:
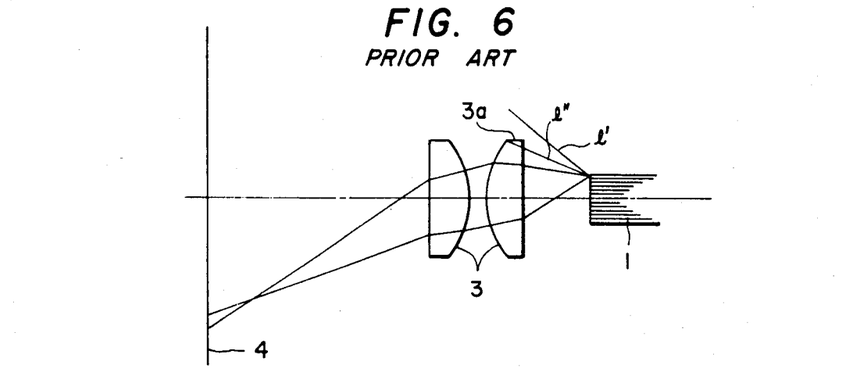
FIG. 6 shows a structure of the optical system in the case where the end face of the light guide in the optical system as shown in FIG. 3 is in a deviated position.
Figure 7:
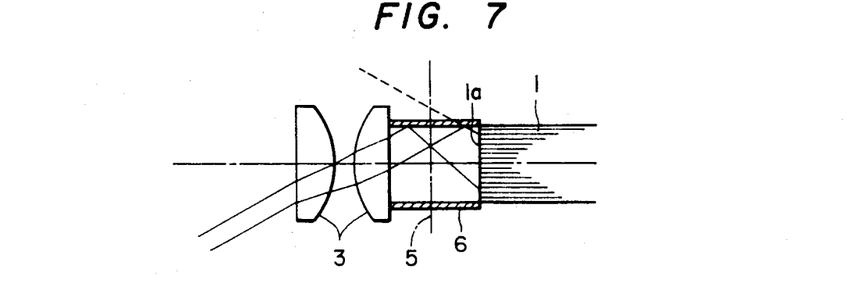
FIG. 7 shows an optical system with which a principle of the present invention is illustrated.

An illumination optical system for an endoscope according to the present invention, as shown in FIG. 7, is so arranged that an exit end face 1a of a light guide 1 is disposed at a position deviated from a surface 5 which is in conjugate with an object surface with respect to a lens system 3 and a cylindrical reflection member 6 whose inner surface is a reflection surface and which has substantially the same diameter as the light guide is disposed between the lens system and the end face of the light guide. Thus, since the end face of the light guide is deviated from the position in conjugate with the object surface, the illumination light on the object surface becomes a uniform illumination because the image of the end face of the light guide is not formed and the net-pattern is blurred and vanishes. Further, as shown in FIG. 6, such rays as 1' and 1" which are deviated from the lens system as a consequence of the deviation of the end face of the light guide from the conjugate surface concerned are reflected at the reflection surface of the cylindrical reflection member 6 so that they can be used as the illumination light. Therefore, it is also possible to prevent a loss of light. Further, since the inner surface on the periphery of the end of the cylindrical reflection member functions as a field stop, the distribution curve of luminous intensity is improved as shown in FIG. 4 but not as shown in FIG. 2.

Figure 15:
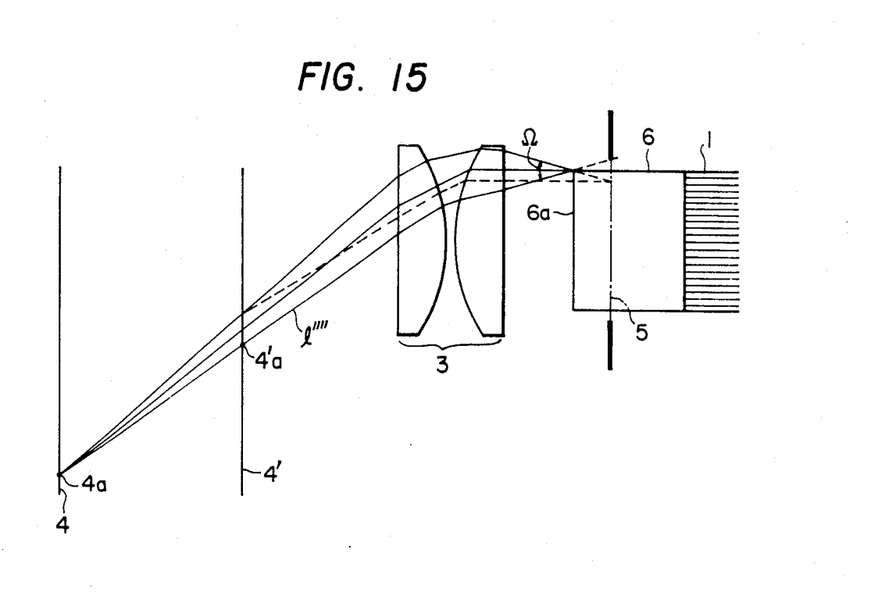
FIG. 15 shows the relation between the position of the object to be illuminated and the field stop and others.

Further details of the distribution curve of luminous intensity are explained hereinafter. In this illumination system in which the cylindrical reflection mirror 6 is disposed between the light guide 1 and the lens system 3 as shown in FIG. 15, the distribution curve of luminous intensity of illumination light will be as shown in FIG. 4 when the end face of the cylindrical reflection mirror 6 at the side of the lens system 3 and the object surface are in a conjugate relation with respect to the lens system 3. However, when the conjugate position is deviated from the object surface, the distribution curve of luminous intensity of illumination light will be slightly deteriorated from that shown in FIG. 4. As a shown in FIG. 15, when the object surface 4 and the end face 6a of the cylindrical reflection mirror 6 are in a conjugate relation with respect to the lens 3, all the rays from the cylindrical reflection mirror 6 which are included in the solid angle $\Omega$ are converged at the outer-periphery 4a of the illumination field at the object surface 4. Therefore, the illumination light has a certain intensity even at the outer-periphery of the illumination field. For example, when the object surface gets closer towards the illumination system and located at 4', the position in conjugate with the object position 4' in the illumination system, that is, the position of the field stop, deviates towards the light guide 1 and locates at such a position as shown by a chain line in FIG. 15. At the same time, the diameter of the field stop increases to the cross point of the lowest positioned ray 1'''' from the outer-periphery of the cylindrical reflection mirror 6 and the field stop 5. Under this state, only the rays reaching the outer-peripheral portion 4a of the illumination field are of the lowest positioned rays. Therefore, the illumination field lacks light at the outer-peripheral portion thereof and becomes lighter towards the center. For such a reason, the condition of the distribution curve of luminous intensity is deteriorated from that shown in FIG. 4. However, since the focal length is extremely short in an extra-wide angle illumination system for an endoscope such as the optical system of the present invention, even if the object position changes there is very small variation in the position of the field stop. Therefore, the distribution curve of luminous intensity explained above is deteriorated in a small amount and is in close proximity to that shown in FIG. 4.

In an illumination optical system according to the present invention as explained above, the amount of the deviation of the end face of the light guide from the conjugate surface can be small in the case where distances to the object are substantially constant. However, where the object involves far and near points, the amount of the deviation must be larger. If the amount of the deviation is too small, the image of the end face of the light guide is formed in an intermediate position between the far points and near points. Therefore, if the distance to the object coincides with the image position, the net-pattern of the image of the end face is observed together with the object and this interferes with the proper observation of the object. For this reason, it is necessary for the image of the end face to be formed outside the range of the distances within which the observation is possible.

As explained above, while retaining the advantages of the projection type system, namely the merits that the distribution curve of luminous intensity is good and light is not lost, the illumination optical system according to the present invention can eliminate the defect of occurrence of a net-pattern illumination, thereby making it possible to obtain a uniform illumination.

Next, the length of the cylindrical reflection member to be used in the illumination system according to the present invention is explained. In order to prevent the appearance of the net-pattern of the end face of the light guide as it stands, while the light from the cores of the respective fibers which form the light guide gradually spreads as it extends away from the end face of the light guide, it is desirable to make an arrangement so that a position at which the diameter C of the section of the spread-out light is more than twice diameter $\phi$ of the fiber (including a cladding portion) locates at the position of a field stop. To this end, assuming that the numerical aperture of the light from the light guide end face is NA' and the spatial conversion distance between the light guide end face and the field stop is a, it is necessary that the following relations be satisfied.

$$C = 2NA' \cdot a$$

$$C \geq 2\phi$$

Then, $$a \geq \phi/NA'$$

Therefore, it is necessary that a be more than $\phi/NA'$ and, if a become smaller than $\phi/NA'$, a net-pattern of the light guide appears on the object. Also, assuming that the refractive index of the inner portion of the cylindrical member is n, the length L of the cylindrical member will be as follows:

$$L = a \cdot n \geq n\phi/NA'.$$

When an object at infinity is illuminated, a conjugate position in relation to the object will be the rear focal point of the lens system. Accordingly, it is necessary that the exit end face of the light guide be located at a point away from the rear focal point of the lens system at least by the distance L since the object is nearer than infinity. It is not necessary that the entire air space between the lens system and the light guide be covered by the cylindrical mirror but necessary that the cylindrical reflection member having at least the length L be disposed therebetween. Also, when the illumination system according to the present invention is used together with an objective lens capable of observing also an object located close by, it is desirable that the end face of the light guide be located rearwardly by at least the distance L from the conjugate surface in relation to the nearest object surface which can be observed through the objective lens. It is to be noted that an air-space may well be provided between the cylindrical reflection member and the end face of the light guide. However, when the air-space is provided, it is necessary to increase the diameter of the cylindrical reflection member so that there will be no leakage of any light therefrom. On the other hand, when the diameter of the cylindrical reflection member becomes larger than that of the lens, there is such an undesirable consequence that the distal end of the endoscope becomes large and, therefore, the above-mentioned air-space should be determined within such a range of the diameter of the cylindrical reflection member which does not permit the lackage of light. Thus, as the diameter of the cylindrical reflection member varies, the size of the field stop changes, but the extent of the illumination area is determined in relation to the extent of the visual field and can be optionally set based on the combination of the magnification of the lens and the diameter of the cylindrical member. Therefore, there is no need to set any special restrictions in the selection of the diameter of the cylindrical member apart from any needs in practical application. Further, there is no problem in positioning the foremost end of the cylindrical member in front of the rear focal point of the lens. The reasons therefor are hereinafter explained. The lens for illumination does not perform any correction of aberrations at all. Thus, when rays enter the lens for illumination from the illumination field side and are reverse-traced, the image surface of the rays at the peripheral portion includes to the lens side to a great extent. Therefore, in practice, if the position of the light source at the peripheral portion is brought towards the lens from the rear focal position of the lens, the rays can be better converged on the object surface to be illuminated. Furthermore, when the conjugate position with respect to the outer-periphery of the illumination field of the object surface comes out to the front of the most rearward surface of the lens 3 (within the lens system) due to the curvature of field, it is not possible to place the end face of the cylindrical reflection member at that position. In such a case, the best distribution curve of luminous intensity can be obtained if the end face of the cylindrical reflection mirror is in tight contact with the lens 3. Further, the same desirable distribution curve of luminous intensity as that shown in FIG. 4 can be obtained if the cylindrical reflection mirror covers at least a part of the lens system 3.

BRIEF DESCRIPTION OF THE DRAWINGS

In these Figures, like parts are designated by like numerals or symbols.

DESCRIPTION OF THE PREFERRED EMBODIMENTS

Next, the preferred examples of the illumination optical system according to the present invention are explained hereunder.

Figure 8:
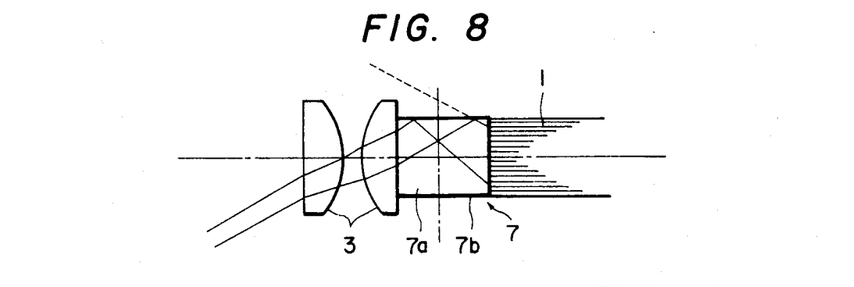
FIGS. 8 through 10 show various embodiments according to the present invention.

FIG. 8 shows an arrangement which is substantially the same as the illustrated by FIG. 7 giving the principle of present invention. As shown in FIG. 8, a mono-fiber 7 (one large fiber comprising a core 7a and a cladding 7b) is inserted between a lens 3 and a light guide 1 as a cylindrical reflection member, and the mono-fiber 7 is joined to the end face of the light guide 1. As the cylindrical reflection member, it can be thought that a cylinder whose inner surface is a mirror surface or a glass rod whose outer surface is plated may be used. However, as compared therewith, the one in which a mono-fiber is used is much more advantageous since such a mono-fiber has a high reflection factor.

Figure 9:
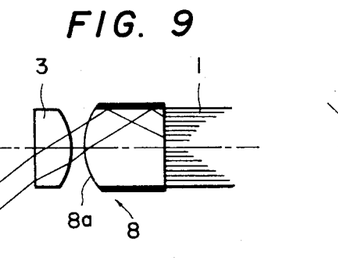

It will be noted from FIG. 9 that a mono-fiber 8 is positioned between the lens 3 and the light guide 1, one end of the mono-fiber 8 being a ground spherical surface 8a and the other end thereof being joined to the end face of the light guide 1. The arrangement according to this embodiment in which the spherical surface 8a of the mono-fiber 8 is made to possess a refracting power provides a lens of a simple structure. This embodiment thus enables not only the simplification of the lens system but also the elimination of the need to use a metal frame and the making of the endoscope slender.

Figure 10:
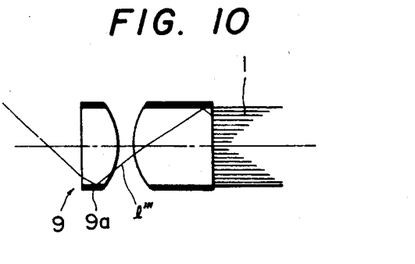

FIG. 10 is a modification of the embodiment shown by FIG. 9, in which the lens 3 of FIG. 9 is substituted by the lens 9 which is formed with the mono-fiber being ground. According to this arrangement, since the light 1''' which reaches the outer surface 9a of the lens 9 is reflected without being absorbed, the illumination light is more effectively utilized.

Figure 16:
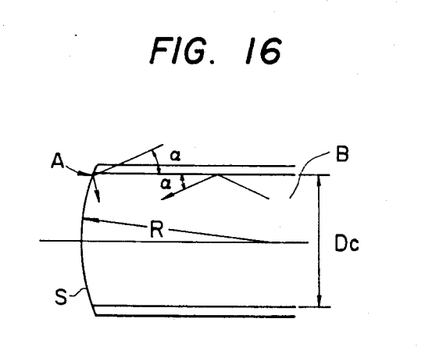
FIG. 16 shows the condition of rays passing through the mono-fiber whose end face is of a curved surface.

In the case where the cylindrical reflection member of a mono-fiber or a glass rod whose end face is a curved surface is used as shown in FIGS. 9 and 10, if the inclination angle of the light which passes through the reflection member is large, there occurs a leakage of the light from the reflection member. That is, as shown in FIG. 16, the rays which pass through the core B penetrate through the cladding if the inclination angle is larger than the value $\alpha_1$ derived from the following equation:

$$\alpha_1 = 90° - \sin^{-1}(n_1/n)$$

where n is the refractive index of the core B and n' is the refractive index of the cladding. Further, it is to be noted that the cladding does not have to be used and, in such a case, n'=1.0 applies to the above equation.

Therefore, the inclination angle of the light passing through the core of the cylindrical reflection member is smaller than the value $\alpha_1$ derived from the above equation. When the rays of the inclination angle $\alpha_1$ come out to the air from the boundary A between the core and the cladding, it is necessary that, for rays to come out of the core without the total reflection at the surface S, the radius curvature R of the surface S be within the following ranges:

$$|R| \geqq \frac{Dc}{2 \sin\left(\sin^{-1}\frac{1}{n} - \alpha_1\right)}$$

where Dc is a diameter of the core.

That is to say that, when the radius curvature R of the surface S does not satisfy the above relation, there is a loss in the amount of the light because the light coming out from the cylindrical reflection member is totally reflected at the surface S. In practice, the rays having an inclination angle $\alpha_1$ are weak in their intensity due to the distribution of the rays from the light source and other factors so that the restriction concerning $|R|$ may be within the ranges of the following formula:

$$|R| \geqq \frac{0.6\, Dc}{2 \sin\left(\sin^{-1}\frac{1}{n} - \alpha_1\right)}$$

If the distribution of the rays from the light source is narrow and the inclination angle of the light which has the maximum inclination in the fiber is $\alpha_2$ ($\alpha_2 < \alpha_1$) the restriction ranges of $|R|$ are as follows:

$$|R| \geqq \frac{Dc}{2 \sin\left(\sin^{-1}\frac{1}{n} - \alpha_2\right)}$$

In practice, the range of $|R|$ will become as follows when the reasons explained above are taken into account:

$$|R| \geqq \frac{0.6\, Dc}{2 \sin\left(\sin^{-1}\frac{1}{n} - \alpha_2\right)}$$

Figure 17:
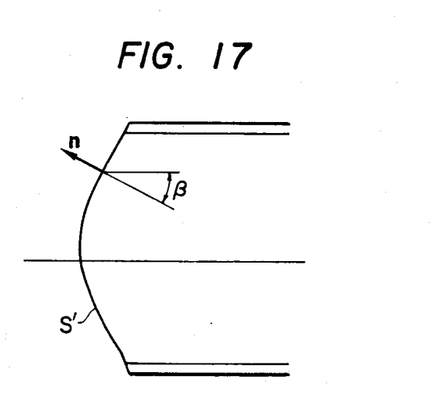
FIG. 17 shows the condition of rays passing through the self-focussing fiber.

Further, the end face of a mono-fiber or a glass rod may well be ground as an aspherical surface. In such a case, as shown in FIG. 17, the angle $\beta$ formed by the normal vector n and the axis of the mono-fiber may be within the following range $$|\beta| \leqq \sin^{-1}(1/n) - \alpha_1$$

In practice, the allowable ranges of $\beta$ are:

$$|\beta| \leqq 2(\sin^{-1}(1/n) - \alpha_1)$$

Detailed numerical values involved in the illumination optical system for an endoscope according to the present invention are given below:

EXAMPLE 1

| | f = 0.955, | ω = 58° |
|---|---|---|
| $r_1 = 5$ | | |
| | $d_1 = 0.9$ | $n_1 = 1.8061$ |
| $r_2 = -1.3$ | | |
| | $d_2 = 0.1$ | |
| $r_3 = 5$ | | |
| | $d_3 = 0.7$ | $n_2 = 1.8061$ |
| $r_4 = -2.3$ | | |
| | $d_4 = 0$ | |
| $r_5 = \infty$ | | |
| | $d_5 = 3.0$ | $n_3 = 1.62$ (mono-fiber) |
| $r_6 = \infty$ | | |

EXAMPLE 1-continued

D = 1.6, L = 2.21, NA' = 0.5

$\phi = 30\mu$, $\dfrac{n\phi}{NA'} = 0.097$

EXAMPLE 2

| | f = 1.035, | ω = 56° |
|---|---|---|
| $r_1 = 2$ | | |
| | $d_1 = 0.8$ | $n_1 = 1.8061$ |
| $r_2 = -2$ | | |
| | $d_2 = 0.1$ | |
| $r_3 = 2$ | | |
| | $d_3 = 3.0$ | $n_2 = 1.62$ (mono-fiber) |
| $r_4 = \infty$ | | |

D = 1.6, L = 2.28, NA' = 0.5

$\phi = 30\mu$, $\dfrac{n\phi}{NA'} = 0.097$

EXAMPLE 3

| | f = 1.34, | ω = 58.4° |
|---|---|---|
| $r_1 = \infty$ | | |
| | $d_1 = 0.5$ | $n_1 = 1.8061$ |
| $r_2 = 2$ | | |
| | $d_2 = 0.5$ | |
| $r_3 = 1.5$ | | |
| | $d_3 = 2.0$ | $n_2 = 1.8061$ |
| $r_4 = -1.5$ | | |
| | $d_4 = 0.5$ | |
| $r_5 = \infty$ | | |
| | $d_5 = 3.0$ | $n_3 = 1.62$ (mono-fiber) |
| $r_6 = \infty$ | | |

D = 1.6, L = 1.78, NA' = 0.5

$\phi = 30\mu$, $\dfrac{n\phi}{NA'} = 0.097$

EXAMPLE 4

| | f = 1.405, | ω = 64° |
|---|---|---|
| $r_1 = 2.696$ | | |
| | $d_1 = 1.2$ | $n_1 = 1.8061$ |
| $r_2 = -2.404$ | | |
| | $d_2 = 0.1$ | |
| $r_3 = 3.2$ | | |
| | $d_3 = 3.0$ | $n_2 = 1.62$ (mono-fiber) |
| $r_4 = \infty$ | | |

D = 2.2, L = 1.306, NA' = 0.5

$\phi = 30\mu$, $\dfrac{n\phi}{NA'} = 0.097$ where
$r_1$ through $r_6$ are radii of curvature of the respective lens surfaces;
$d_1$ through $d_5$ are the axial thicknesses of the respective lenses or the axial air spaces therebetween;
$n_1$ through $n_3$ are the refractive indices of the respective lenses; and D is the diameter of the light guide, respectively, r, d and n having been shown with the inclusion of a mono-fiber as the cylindrical reflection member. The units of length are in mm.

Figure 11:
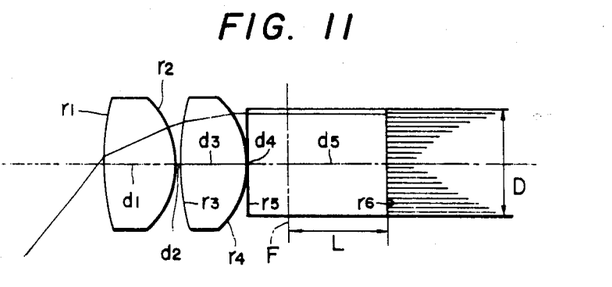
FIGS. 11 through 14 show optical systems corresponding to the numerical examples of the present invention.

In the above numerical examples, the example 1 relates to such an optical system as shown in FIG. 11 in which a cylindrical reflection member of a mono-fiber is disposed between the light guide and the lens system composed of two convex lenses.

Figure 12:
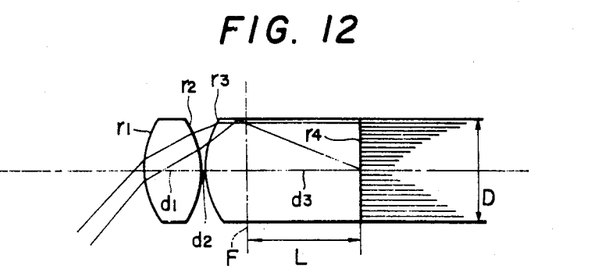

The example 2 relates to an optical system as shown in FIG. 12 in which a mono-fiber whose one end is a ground spherical surface is disposed between a single positive lens and the light guide.

Figure 13:
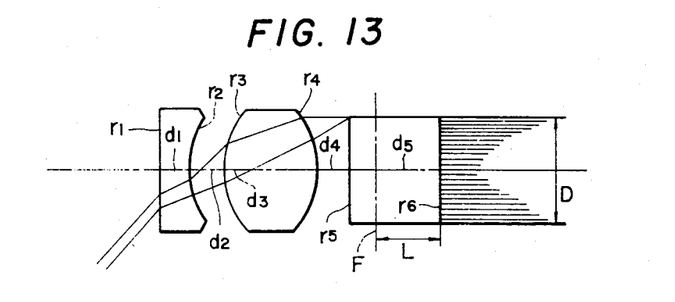

The example 3 relates to an optical system as shown in FIG. 13 in which a mono-fiber is disposed between the light guide and the lens system composed of a concave lens and a convex lens.

Figure 14:
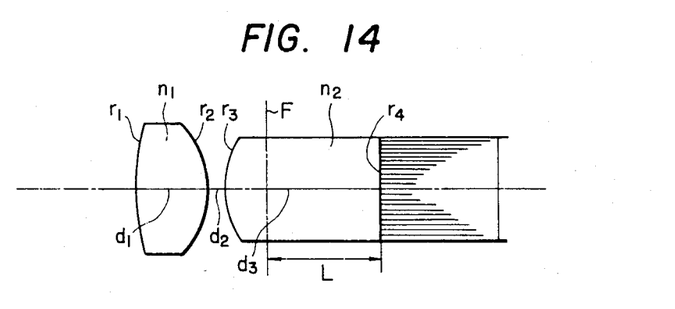

The example 4 relates to an optical system as shown in FIG. 14 wherein a mono-fiber one end of which is a ground spherical surface is disposed between a single positive lens and the light guide.

Symbol F in FIGS. 11 through 14 represent the rear focal plane.

The above explanation has been directed mainly to the embodiments utilizing the reflection member of a roundcylindrical shape. However, the reflection member is not restricted to a round-shape, but can well be in such a shape that the section of the member is square or that the cylindrical reflection member is tapered with one end thereof being smaller than the other end.

The cylindrical reflection member may adopt a self-focussing fiber, etc. besides a cylindrical reflection mirror, a mono-fiber, a glass rod, etc.

We claim:

1. An illumination optical system for an endoscope comprising a light guide comprising a fiber bundle formed by bundling up a number of optical fibers each of which can transmit the light at the same time, a positive lens system disposed in front of said light guide, and a cylindrical reflection member comprising a mono-fiber arranged between the said lens system and an exit end face of the said light guide and having substantially the same diameter as the said light guide, an end face of the said mono-fiber at the lens side being a curved surface, and in which the radius of curvature R of the said curved surface satisfies the following formula:

$$|R| \geq \frac{0.6\, Dc}{2 \sin\left( \sin^{-1}\frac{1}{n} - \alpha_1 \right)}$$

where
Dc is the diameter of the mono-fiber,
n is the refractive index of the mono-fiber, and
$\alpha_1$ is the angle formed by the ray having the widest angle of view with the axis of the mono-fiber, respectively.

2. An illumination optical system for an endoscope comprising a light guide comprising a fiber bundle formed by bundling up a number of optical fibers each of which can transmit the light at the same time, a positive lens system disposed in front of said light guide, and a cylindrical reflection member arranged between the said lens system and an exit end face of the said light guide and having substantially the same diameter as the said light guide, at least one end face of the said mono-fiber at the lens side being a curved surface, and in which the radius of curvature R of the said curved surface satisfies the following formula:

$$|R| \geq \frac{0.6\, Dc}{2 \sin\left( \sin^{-1}\frac{1}{n} - \alpha_1 \right)}$$

where
Dc is the diameter of the mono-fiber,
n is the refractive index of the mono-fiber, and
$\alpha_1$ is the angle formed by the ray having the widest angle of view with the axis of the mono-fiber, respectively.

3. An illumination optical system for an endoscope comprising a light guide comprising a fiber bundle formed by bundling up a number of optical fibers each of which can transmit the light at the same time, a positive lens system disposed in front of said light guide, and a cylindrical reflection member comprising a mono-fiber arranged between the said lens system and an exit end face of the said light guide and having substantially the same diameter as the said light guide, an end face of the said mono-fiber at the lens side being a curved surface, each lens of the said positive lens system being made of a mono-fiber at least one end face of which is of a curved surface, and in which the radius of curvature R of the said curved surface satisfies the following formula:

$$|R| \geq \frac{0.6\, Dc}{2 \sin\left( \sin^{-1}\frac{1}{n} - \alpha_1 \right)}$$

where
Dc is the diameter of the mono-fiber,
n is the refractive index of the mono-fiber, and
$\alpha_1$ is the angle formed by the ray having the widest angle of view with the axis of the mono-fiber, respectively.

4. An illumination optical system for an endoscope comprising a light guide comprising a fiber bundle formed by bundling up a number of optical fibers each of which can transmit the light at the same time, a positive lens system disposed in front of said light guide, and a cylindrical reflection member comprising a mono-fiber arranged between the said lens system and an exit end face of the said light guide and having substantially the same diameter as the said light guide, an end face of the said mono-fiber at the lens side being a curved surface, and in which the radius of curvature R of the said curved surface satisfies the following formula:

$$|R| \geq \frac{0.6\, Dc}{2 \sin\left( \sin^{-1}\frac{1}{n} - \alpha_2 \right)}$$

where
Dc is the diameter of the mono-fiber,
n is the refractive index of the mono-fiber and
$\alpha_1$ in the angle formed by the ray from the light source having the widest angle with the axis of the mono-fiber, respectively.

5. An illumination optical system for an endoscope comprising a light guide comprising a fiber bundle formed by bundling up a number of optical fibers each of which can transmit the light at the same time, a positive lens system disposed in front of said light guide, and a cylindrical reflection member arranged between the said lens system and an exit end face of the said light guide and having substantially the same diameter as the said light guide, each lens of the said lens system being made of a mono-fiber at least one end face of which is of a curved surface, and in which the radius of curvature R of the said curved surface satisfies the following formula:

$$|R| \geqq \frac{0.6 \, Dc}{2 \sin\left(\sin^{-1}\frac{1}{n} - \alpha_2\right)}$$

where

DC is the diameter of the mono-fiber, n is the refractive index of the mono-fiber, and $\alpha_2$ in the angle formed by the ray from the light source having the widest angle with the axis of the mono-fiber, respectively.

6. An illumination optical system for an endoscope comprising a light guide comprising a fiber bundle formed by bundling up a number of optical fibers each of which can transmit the light at the same time, a positive lens system disposed in front of said light guide, and a cylindrical reflection member comprising a mono-fiber arranged between the said lens system and an exit end face of the said light guide, an end face of the said mono-fiber at the lens side being a curved surface, each lens of the said lens system being made of a mono-fiber at least one end face of which is of a curved surface, and in which the radius of curvature R of the said curved surface satisfies the following formula:

$$|R| \geqq \frac{0.6 \, Dc}{2 \sin\left(\sin^{-1}\frac{1}{n} - \alpha_2\right)}$$

where

Dc is the diameter of the mono-fiber, n is the refractive index of the mono-fiber, and $\alpha_2$ in the angle formed by the ray from the light source having the widest angle with the axis of the mono-fiber, respectively.

7. An illumination optical system for an endoscope comprising a light guide comprising a fiber bundle formed by bundling up a number of optical fibers each of which can transmit the light at the same time, a positive lens system disposed in front of said light guide, and a cylindrical reflection member comprising a mono-fiber arranged between the said lens system and an exit end face of the said light guide and having substantially the same diameter as the said light guide, an end face of the said mono-fiber at the lens side being a curved surface, and in which the said curved surface is of an aspherical surface and the angle $\beta$ which is formed by the normal vector of the said aspherical surface with the axis of the mono-fiber satisfies the following formula:

$$|\beta| \leqq 2(\sin^{-1}(1/n) - \alpha_1)$$

where $\alpha_1$ is the angle formed by the ray having the widest angle of view with the axis of the mono-fiber, respectively.

8. An illumination optical system for an endoscope comprising a light guide comprising a fiber bundle formed by bundling up a number of optical fibers each of which can transmit the light at the same time, a positive lens system disposed in front of said light guide, and a cylindrical reflection member arranged between the said lens system and an exit end face of the said light guide and having substantially the same diameter as the said light guide, each lens of the said lens system being made of a mono-fiber at least one end face of which is of a curved surface, and in which the said curved surface is of an aspherical surface and the angle $\beta$ which is formed by the normal vector of the said aspherical surface with the axis of the mono-fiber satisfies the following formula:

$$|\beta| \leqq 2(\sin^{-1}(1/n) - \alpha_1)$$

where $\alpha_1$ is the angle formed by the ray having the widest angle of view with the axis of the mono-fiber, respectively.

9. An illumination optical system for an endoscope comprising a light guide comprising a fiber bundle formed by bundling up a number of optical fibers each of which can transmit the light at the same time, a positive lens system disposed in front of said light guide, and a cylindrical reflection member comprising a mono-fiber arranged between the said lens system and an exit end face of the said light guide and having substantially the same diameter as the said light guide, an end face of the said mono-fiber at the lens side being a curved surface, each lens of the said lens system being made of a mono-fiber at least one end face of which is a curved surface, and in which the said curved surface is of an aspherical surface and the angle $\beta$ which is formed by the normal vector of the said aspherical surface with the axis of the mono-fiber satisfies the following formula:

$$|\beta| \leqq 2(\sin^{-1}(1/n) - \alpha_1)$$

where $\alpha_1$ is the angle formed by the ray having the widest angle of view with the axis of the mono-fiber, respectively.

10. An illumination optical system for an endoscope comprising a light guide comprising a fiber bundle formed by bundling up a number of optical fibers each of which can transmit the light at the same time, a positive lens system disposed in front of said light guide, and a cylindrical reflection member comprising a mono-fiber arranged between the said lens system and an exit end face of the said light guide and having substantially the same diameter as the said light guide, and in which the said lens system is composed of two convex lenses, and which has the following data:

| | | |
|---|---|---|
| $r_1 = 5$ | $f = 0.955,$ | $\omega = 58°$ |
| $r_2 = -1.3$ | $d_1 = 0.9$ | $n_1 = 1.8061$ |
| $r_3 = 5$ | $d_2 = 0.1$ | |
| $r_4 = -2.3$ | $d_3 = 0.7$ | $n_2 = 1.8061$ |
| $r_5 = \infty$ | $d_4 = 0$ | |
| $r_6 = \infty$ | $d_5 = 3.0$ | $n_3 = 1.62$ (mono-fiber) |
| | $D = 1.6, \quad L = 2.21$ | $NA' = 0.5$ |
| | $\phi = 30\mu, \quad \dfrac{n\phi}{NA'} = 0.097$ | | where $r_1, r_2 \ldots$ are radii of curvature of the respective surfaces of the lens system and the mono-fiber;

$d_1, d_2 \ldots$ are the axial thicknesses of the respective lenses of the lens system or the mono-fiber or the axial air spaces therebetween;

$n_1$ through $n_3$ are refractive indices of the respective lenses or the mono-fiber;

D is the diameter of the light guide; and

NA' is the numerical aperture of the light from the end face of the light guide, respectively.

11. An illumination optical system for an endoscope comprising a light guide comprising a fiber bundle formed by bundling up a number of optical fibers each of which can transmit the light at the same time, a positive lens system disposed in front of said light guide, and a cylindrical reflection member comprising a mono-fiber arranged between the said lens system and an exit end face of the said light guide and having substantially the same diameter as the said light guide, an end face of the said mono-fiber at the lens side being a curved surface, and in which the said lens system is composed of convex lenses, and which has the following data:

| | $f = 1.035,$ | $\omega = 56°$ | |
|---|---|---|---|
| $r_1 = 2$ | | | |
| | $d_1 = 0.8$ | $n_1 = 1.8061$ | |
| $r_2 = -2$ | | | |
| | $d_2 = 0.1$ | | |
| $r_3 = 2$ | | | |
| | $d_3 = 3.0$ | $n_2 = 1.62$ (mono-fiber) | |
| $r_4 = \infty$ | | | |
| | $D = 2.2,$ | $L = 1.306,$ | $NA' = 0.5$ |
| | $\phi = 30\mu,$ | $\dfrac{n\phi}{NA'} = 0.097$ | | where $r_1, r_2 \ldots$ are radii of curvature of the respective surfaces of the lens system and the mono-fiber;

$d_1, d_2 \ldots$ are the axial thicknesses of the respective lenses of the lens system or the mono-fiber or the axial air spaces therebetween;

$n_1$ through $n_3$ are refractive indices of the respective lenses or the mono-fiber;

D is the diameter of the light guide; and

NA' is the numerical aperture of the light from the end face of the light guide, respectively.

12. An illumination optical system for an endoscope comprising a light guide comprising a fiber bundle formed by bundling up a number of optical fibers each of which can transmit the light at the same time, a positive lens system disposed in front of said light guide, and a cylindrical reflection member comprising a mono-fiber arranged between the said lens system and an exit end face of the said light guide and having substantially the same diameter as the said light guide, and in which the said lens system is composed of a concave lens and a convex lens, and which has the following data:

| | $f = 1.34$ | $\omega = 58.4°$ |
|---|---|---|
| $r_1 = \infty$ | | |
| | $d_1 = 0.5$ | $n_1 = 1.8061$ |
| $r_2 = 2$ | | |
| | $d_2 = 0.5$ | |
| $r_3 = 1.5$ | | |
| | $d_3 = 2.0$ | $n_2 = 1.8061$ |
| $r_4 = -1.5$ | | |
| | $d_4 = 0.5$ | |
| $r_5 = \infty$ | | |
| | $d_5 = 3.0$ | $n_3 = 1.62$ (mono-fiber) |
| $r_6 = \infty$ | | |
| | $D = 1.6,$ $L = 1.78,$ | $NA' = 0.5$ |
| | $\phi = 30\mu,$ $\dfrac{n\phi}{NA'} = 0.097$ | | where $r_1, r_2 \ldots$ are radii of curvature of the respective surfaces of the lens system and the mono-fiber;

$d_1, d_2 \ldots$ are the axial thicknesses of the respective lenses of the lens system or the mono-fiber or the axial air spaces therebetween;

$n_1$ through $n_3$ are refractive indices of the respective lenses or the mono-fiber;

D is the diameter of the light guide; and

NA' is the numerical aperture of the light from the end face of the light guide, respectively.

13. An illumination optical system for an endoscope comprising a light guide comprising a fiber bundle formed by bundling up a number of optical fibers each of which can transmit the light at the same time, a positive lens system disposed in front of said light guide, and a cylindrical reflection member comprising a mono-fiber arranged between the said lens system and an exit end face of the said light guide and having substantially the same diameter as the said light guide, an end face of the said mono-fiber at the lens side being a curved surface, and in which the said lens system is composed of convex lenses, and which has the following data:

| | $f = 1.405$ | $\omega = 64°$ | |
|---|---|---|---|
| $r_1 = 2.696$ | | | |
| | $d_1 = 1.2$ | $n_1 = 1.8061$ | |
| $r_2 = -2.404$ | | | |
| | $d_2 = 0.1$ | | |
| $r_3 = 3.2$ | | | |
| | $d_3 = 3.0$ | $n_2 = 1.62$ (mono-fiber) | |
| $r_4 = \infty$ | | | |
| | $D = 2.2,$ | $L = 1.306,$ | $NA' = 0.5$ |
| | $\phi = 30\mu,$ | $\dfrac{n\phi}{NA'} = 0.097$ | | where $r_1, r_2 \ldots$ are radii of curvature of the respective surfaces of the lens system and the mono-fiber;

$d_1, d_2 \ldots$ are the axial thicknesses of the respective lenses of the lens system or the mono-fiber or the axial air spaces therebetween;

$n_1$ through $n_3$ are refractive indices of the respective lenses or the mono-fiber;

D is the diameter of the light guide; and

NA' is the numerical aperture of the light from the end face of the light guide, respectively.

* * * * *